US010593296B2

(12) United States Patent
Liu

(10) Patent No.: US 10,593,296 B2
(45) Date of Patent: Mar. 17, 2020

(54) ELECTRONIC DEVICE AND METHOD FOR SELECTIVELY ILLUMINATING REGIONS OF A DISPLAY SCREEN OF THE ELECTRONIC DEVICE

(71) Applicant: ROYOLE CORPORATION, Fremont, CA (US)

(72) Inventor: Zihong Liu, Fremont, CA (US)

(73) Assignee: ROYOLE CORPORATION, Fremont, CA (US)

( * ) Notice: Subject to any disclaimer, the term of this patent is extended or adjusted under 35 U.S.C. 154(b) by 0 days.

(21) Appl. No.: 16/123,847

(22) Filed: Sep. 6, 2018

(65) Prior Publication Data

US 2019/0005922 A1 Jan. 3, 2019

Related U.S. Application Data

(63) Continuation-in-part of application No. 14/681,785, filed on Apr. 8, 2015, now abandoned.

(Continued)

(51) Int. Cl.

*G09G 5/14* (2006.01)
*G09G 3/34* (2006.01)

(Continued)

(52) U.S. Cl.

CPC ............. *G09G 5/14* (2013.01); *G09G 3/3225* (2013.01); *G09G 3/3426* (2013.01);

(Continued)

(58) Field of Classification Search

CPC .. G09G 3/3208; G09G 3/3225; G09G 3/3406; G09G 3/342; G09G 3/3426;

(Continued)

(56) References Cited

U.S. PATENT DOCUMENTS

2002/0175887 A1 11/2002 Yamazaki
2004/0051706 A1* 3/2004 Nakano ................ G09G 3/3666 345/204

(Continued)

FOREIGN PATENT DOCUMENTS

CN 102143275 8/2011
CN 102346644 2/2012

(Continued)

*Primary Examiner* — Keith L Crawley
(74) *Attorney, Agent, or Firm* — Hauptman Ham, LLP

(57) ABSTRACT

A method for controlling a display screen includes the follows: detecting a first event that will trigger partially turning on of the display screen while the display screen is in an off state; acquiring a predetermined user interface to be displayed according to the first event; determining whether the first event belongs to one of an active event and a passive event; turning on a first display area to display the predetermined user interface when the first event is the active event, where the predetermined user interfaces associated with a plurality of active events are all displayed on the first display area; and turning on a second display area to display the predetermined user interface when the first event is the passive event, where the predetermined user interfaces associated with a plurality of passive events are all displayed on the second display area. A related electronic device is also provided.

20 Claims, 8 Drawing Sheets

Related U.S. Application Data

(60) Provisional application No. 62/046,887, filed on Sep. 5, 2014.

(51) Int. Cl.
*G09G 3/36* (2006.01)
*G09G 3/3225* (2016.01)

(52) U.S. Cl.
CPC ........... *G09G 3/3648* (2013.01); *G09G 3/344* (2013.01); *G09G 2320/0686* (2013.01); *G09G 2320/10* (2013.01); *G09G 2330/021* (2013.01); *G09G 2330/023* (2013.01); *G09G 2330/026* (2013.01); *G09G 2330/027* (2013.01); *G09G 2354/00* (2013.01)

(58) Field of Classification Search
CPC ........ G09G 3/344; G09G 3/3648; G09G 5/14; G09G 2310/04; G09G 2320/0686; G09G 2320/10; G09G 2330/021; G09G 2330/022; G09G 2330/023; G09G 2330/026; G09G 2330/027; G09G 2354/00; G09G 2380/14; G06F 1/32; G06F 1/3203; G06F 1/3206; G06F 1/3234; G06F 1/3265
See application file for complete search history.

(56) References Cited

U.S. PATENT DOCUMENTS

| | | | | |
|---|---|---|---|---|
| 2004/0095522 | A1 | 5/2004 | Lee | |
| 2005/0057539 | A1 | 3/2005 | Ong | |
| 2006/0132474 | A1 | 6/2006 | Lam | |
| 2010/0164857 | A1 | 7/2010 | Liu | |
| 2011/0181611 | A1 | 7/2011 | Zhang | |
| 2011/0261087 | A1 | 10/2011 | Bahk | |
| 2012/0077554 | A1 | 3/2012 | Ahn et al. | |
| 2014/0092140 | A1 | 4/2014 | Wadhwa | |
| 2014/0180595 | A1* | 6/2014 | Brumback | A61B 5/0015 702/19 |
| 2014/0344608 | A1 | 11/2014 | Wang | |
| 2015/0061988 | A1 | 3/2015 | Galu, Jr. | |
| 2015/0294627 | A1 | 10/2015 | Yoo | |
| 2015/0362980 | A1* | 12/2015 | Tripathi | G06F 1/3287 713/324 |
| 2016/0291370 | A1* | 10/2016 | Foo | G02F 1/13318 |

FOREIGN PATENT DOCUMENTS

| | | |
|---|---|---|
| CN | 103135742 | 6/2013 |
| CN | 103345906 | 10/2013 |

* cited by examiner

ELECTRONIC DEVICE AND METHOD FOR SELECTIVELY ILLUMINATING REGIONS OF A DISPLAY SCREEN OF THE ELECTRONIC DEVICE

CROSS-REFERENCE TO RELATED APPLICATIONS

This application is a continuation-in-part application of U.S. application Ser. No. 14/681,785, field on Apr. 8, 2015, which is based upon and claims the benefit of priority from Provisional Application No. 62/046,887, filed on Sep. 5, 2014, the entire contents of which are incorporated herein by reference.

TECHNICAL FIELD

The present disclosure relates to a method for controlling a display and, more particularly, to an electronic device and a method for controlling a display screen of the electronic device to partially power on.

BACKGROUND

With the development of mobile technology, mobile devices, such as smart phones or tablets, have become more and more important in people's daily life. A mobile device is usually powered by a built-in battery. Due to the nature of the mobile device, the capacity of the built-in battery is often compromised to, for example, achieve better mobility. Therefore, power consumption needs to be taken into consideration when designing a mobile device.

A mobile device is equipped with a display screen to display information or contents. Usually, a fair amount of power is consumed by the display screen. Sometimes, for example, the display screen may consume about 70%-80% of the total power of the mobile device. Therefore, a battery life of the mobile device is often affected by the display screen. In the conventional technology, when the mobile device needs to display a piece of information or certain contents, the entire display screen needs to be powered on. Sometimes, the information or content that needs to be displayed only occupies a small portion of the display screen, and thus the rest of the display screen is not utilized but still consumes power. As a result, a lot of power is wasted, and the battery life of the mobile device is reduced.

To reduce the power consumption by a display screen, a mobile device may provide an option to reduce the brightness of the entire display screen. However, reducing the brightness may also reduce the readability of the contents displayed on the display screen, and thus affects the user experience.

SUMMARY

Embodiments of the present disclosure provide an electronic device and a method for controlling a display screen of the electronic device.

According to a first aspect, the embodiments of the present disclosure provide a method for controlling a display screen of an electronic device. The method includes the following: detecting a first event that will trigger partially turning on of the display screen while the display screen is in an off state; acquiring a predetermined user interface to be displayed according to the first event; determining whether the first event belongs to one of the following: (1) an active event resulting from a user operation on the electronic device, and (ii) a passive event that is independent of a user operation on the electronic device; turning on a first display area of the display screen to display the acquired predetermined user interface, based on a determination that the first event is the active event, wherein the first display area corresponds to a plurality of active events, and the predetermined user interfaces associated with the plurality of active events are all displayed on the first display area; and turning on a second display area of the display screen to display the acquired predetermined user interface, based on a determination that the first event is the passive event, wherein the second display area corresponds to a plurality of passive events, and the predetermined user interfaces associated with the plurality of passive events are all displayed on the second display area.

According to a second aspect, the embodiments of the present disclosure provide an electronic device. The electronic device includes a display screen, a processor and a computer readable storage. The computer readable storage is coupled to the processor and stores at least one computer executable instruction thereon, which when executed by the processor, cause the processor to carry out actions, including: detecting a first event that will trigger partially turning on of the display screen while the display screen is in an off state; acquiring a predetermined user interface to be displayed according to the first event; determining whether the first event belongs to one of the following: (1) an active event resulting from a user operation on the electronic device, and (ii) a passive event that is independent of a user operation on the electronic device; turning on a first display area of the display screen to display the acquired predetermined user interface, based on a determination that the first event is the active event, wherein the first display area corresponds to a plurality of active events, and the predetermined user interfaces associated with the plurality of active events are all displayed on the first display area; and turning on a second display area of the display screen to display the acquired predetermined user interface, based on a determination that the first event is the passive event, wherein the second display area corresponds to a plurality of passive events, and the predetermined user interfaces associated with the plurality of passive events are all displayed on the second display area.

According to a third aspect, the embodiments of the present disclosure provide a non-transitory computer readable storage medium. The non-transitory computer readable storage medium is configured to store computer programs which, when executed by a processor, cause the processor to carry out actions: detecting a first event that will trigger partially turning on of the display screen while the display screen is in an off state; acquiring a predetermined user interface to be displayed according to the first event; determining whether the first event belongs to one of the following: (1) an active event resulting from a user operation on the electronic device, and (ii) a passive event that is independent of a user operation on the electronic device; turning on a first display area of the display screen to display the acquired predetermined user interface, based on a determination that the first event is the active event, wherein the first display area corresponds to a plurality of active events, and the predetermined user interfaces associated with the plurality of active events are all displayed on the first display area; and turning on a second display area of the display screen to display the acquired predetermined user interface, based on a determination that the first event is the passive event, wherein the second display area corresponds to a plurality of passive events, and the predetermined user interfaces associated with the plurality of passive events are all displayed on the second display area.

Features and advantages consistent with the disclosure will be set forth in part in the description which follows, and in part will be obvious from the description, or may be learned by practice of the disclosure. Such features and advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

In order to enable those skilled in the art to better understand solutions of the present disclosure, technical solutions in embodiments of the present disclosure will be described clearly and completely hereinafter with reference to the accompanying drawings in the embodiments of the present disclosure. Apparently, the described embodiments are merely some rather than all embodiments of the present disclosure. All other embodiments obtained by those of ordinary skill in the art based on the embodiments of the present disclosure without creative efforts shall fall within the protection scope of the present disclosure.

The terms “first”, “second”, and the like used in the specification, the claims, and the accompany drawings of the present disclosure are used to distinguish different objects rather than describe a particular order. The terms “include”, “comprise”, and “have” as well as variations thereof are intended to cover non-exclusive inclusion. For example, a process, method, system, product, or apparatus including a series of steps or units is not limited to the listed steps or units. On the contrary, it can optionally include other steps or units that are not listed; alternatively, other steps or units inherent to the process, method, product, or device can be included either.

The term “embodiment” or “implementation” referred to herein means that a particular feature, structure, or characteristic described in conjunction with the embodiment may be contained in at least one embodiment of the present disclosure. The phrase appearing in various places in the specification does not necessarily refer to the same embodiment, nor does it refer to an independent or alternative embodiment that is mutually exclusive with other embodiments. It is expressly and implicitly understood by those skilled in the art that an embodiment described herein may be combined with other embodiments.

Embodiments consistent with the present disclosure provide an electronic device and a method for controlling a display screen of the electronic device to partially power on.

Figure 1:
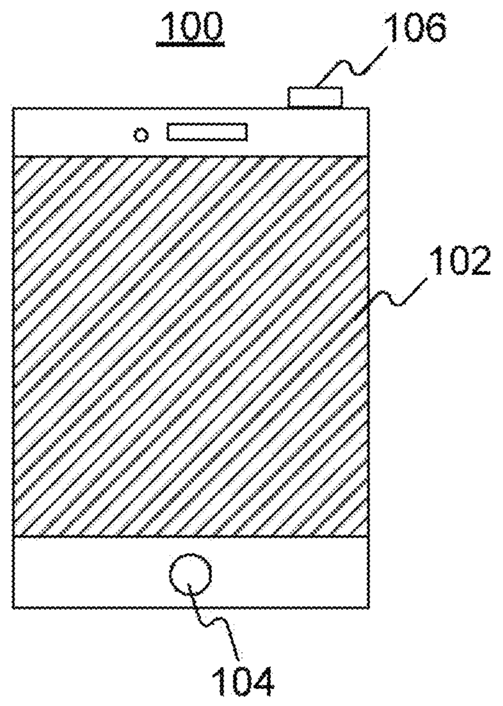
FIG. 1 schematically shows an electronic device with its display screen being in an off state according to an exemplary embodiment.

FIG. 1 schematically shows an electronic device 100 according to an embodiment of the present disclosure. The electronic device 100 includes a display screen 102, a control button 104, and a power button 106.

The display screen 102 is configured to display information or contents, and may be, for example, an LCD screen, an organic light-emitting diode (OLED) (such as a passive-matrix OLED (PMOLED) or an active-matrix OLED (AMOLED)) screen, or an e-ink screen. In some embodiments, the display screen 102 is a touch screen. The display screen 102 may be turned on and off manually, and may automatically enter into an off state from an on state when the electronic device 100 has been idle for a certain period of time.

The control button 104 may be a mechanical button. A user may press on the control button 104 to input a control command, such as turning on the display screen 102, to the electronic device 100. In some embodiments, the control button 104 may include a touch sensor, configured to generate the control command when sensing a touch. The control button 104 may include other sensors to receive various signals. In some embodiments, a finger-print reader may be integrated in the control button 104.

The power button 106 is configured to turn on and off the electronic device 100. For example, the electronic device 100 may be turned on and off by pressing and holding the power button 106 for a certain period of time. In some embodiments, a single pressing on the power button 106 may also turn on and off the display screen 102.

It should be noted that, in some embodiments, the control button 104 and the power button 106 may also be integrated into one button, which is configured to generate a first control command when it receives a first user operation such as a single pressing on the integrated button, in order to turn on/turn off the display screen 102; and generate a second control command when it receives a second user operation such as pressing and holding the integrated button for a certain period of time, in order to turn on/turn off the electronic device 100.

Figure 2:
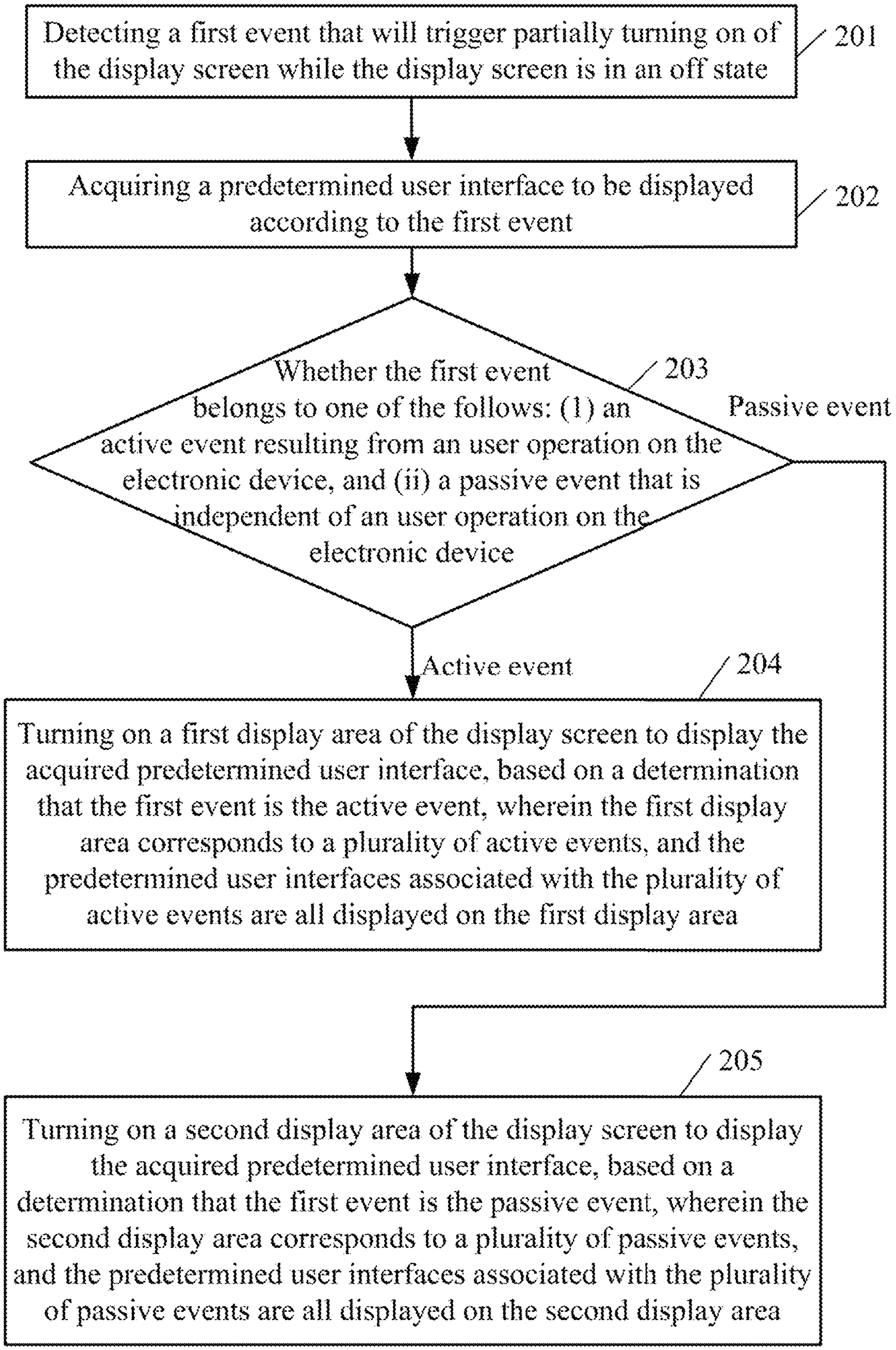
FIG. 2 is a flow chart showing a method for controlling a display screen of the electronic device according to an exemplary embodiment.

FIG. 2 is a flow chart showing an exemplary method 200 according to an embodiment of the present disclosure for controlling a display screen, such as the display screen 102 in the electronic device 100. As illustrated in FIG. 2, the method for controlling a display screen begins at block 201.

At block 201, a first event that will trigger partially turning on of the display screen 102 is detected while the display screen 102 is in an off state.

Figure 3A:
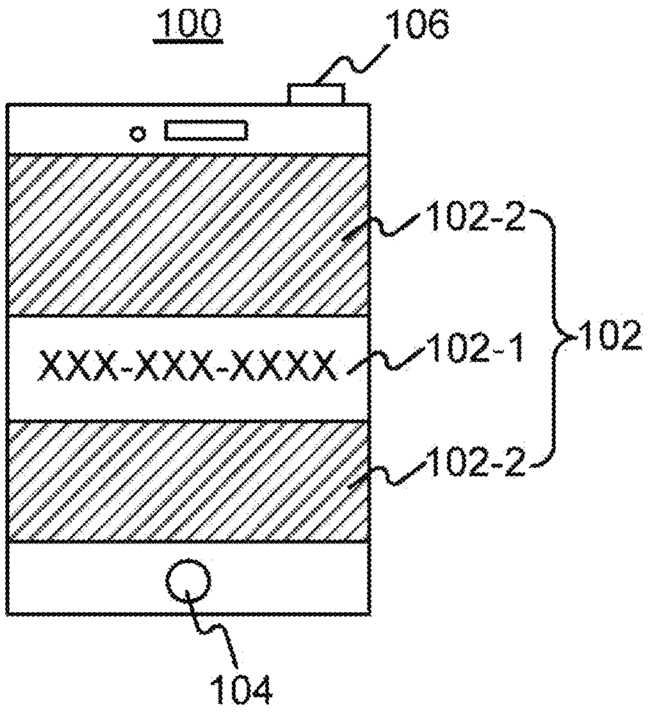
FIGS. 3A and 3B schematically show states of the electronic device when the display screen of the electronic device is partially turned on according to exemplary embodiments.

In the embodiment of the present disclosure, whether the display screen 102 is partially turned on may depend on the detected event. For example, when the electronic device 100 detects an incoming call while the display screen 102 is in the off state, besides outputting a ringing or vibration, the electronic device 100 may also need to display at least one of a phone number and a contact name that is associated with the incoming call on the display screen 102. That is, the electronic device 100 receives a trigger signal to display a piece of information including at least one of the phone number and the contact name. The electronic device 100 determines that only a small portion, such as about 10% or even less, of the entire display screen 102 is needed to display the phone number and/or the contact name. As a result, only the portion of the display screen 102 that is needed to display the phone number and/or contact name is turned on to display such information to the user. The rest of the display screen 102 is kept off. FIG. 3A schematically illustrates this scenario, in which one portion 102-1 of the display screen 102 is turned on to display the phone number and/or contact name, and other portions 102-2 of the display screen 102 are kept off to save power.

At block 202, a predetermined user interface to be displayed is acquired according to the first event.

In the embodiment of the present disclosure, different predetermined user interfaces may be associated with different detected events. For example, when a user presses on the control button 104 or the power button 106 for one time while the display screen 102 is in the off state, that is, a single press event on the control button 104 or the power button 106 of the electronic device 100 is detected, then a predetermined user interface including predetermined information such as a current time, a current date, a remaining battery capacity, a virtual key pad, a sliding bar for unlocking the electronic device 100, and so on, may be acquired. Alternatively, when the electronic device 100 detects an incoming call while the display screen 102 is in the off state, a predetermined user interface including at least one of a phone number and a contact name associated with the incoming call may be acquired.

At block 203, the electronic device 100 determines whether the first event belongs to one of the following: (1) an active event resulting from a user operation on the electronic device, and (ii) a passive event that is independent of a user operation on the electronic device. If the first event is the active event, the operation at block 204 is performed. If the first event is the passive event, the operation at block 205 is performed.

In the embodiment of the present disclosure, the active event and the passive event detected while the display screen 102 is in the off state may trigger the partially turning on of the display screen 102. The active event refers to an event resulting from the user's operation such as a press on the control button 104 or the power button 106 for one time, a press and long hold on the control button 104 or the power button 106, and so on. The passive event refers to an event that is independent of a user operation on the electronic device, for example, a calendar reminder or a notification message generated by an application running on the electronic device 100, or an incoming call or a text message received by the application from another electronic device.

At block 204, a first display area of the display screen is turned on to display the acquired predetermined user interface, wherein the first display area corresponds to a plurality of active events, and the predetermined user interfaces associated with the plurality of active events are all displayed on the first display area.

At block 205, a second display area of the display screen is turned on to display the acquired predetermined user interface, wherein the second display area corresponds to a plurality of passive events, and the predetermined user interfaces associated with the plurality of passive events are all displayed on the second display area.

In the embodiment of the present disclosure, the location of the first display area is different from that of the second display area, and the sizes of the first display area and the second display area are both smaller than that of an entire display area of the display screen 102. That is, when the first display area or the second display area is turned on, at least a portion of the display screen 102 is kept off. Therefore, the turned on display area may consume less power than a full-size display screen 102, so as to conserve power and yet allow the user to see and/or use at least a portion of the display screen 102.

It should be understood that, in the case that the location of the first display area is different from that of the second display area, the first display area or the second display area may locate at an upper half, a bottom half, a central area, a left half, a right half, a top fringe, a bottom fringe, an upper left corner, an upper right corner, a lower left corner or a lower right corner of the display screen 102.

For example, as illustrated in FIG. 3A, the second display area locates in a central portion 102-1 of the display screen 102 and is turned on to display a predetermined user interface (such as an interface showing a phone number) associated with a detected active event (such as an incoming call), and other portions 102-2 of the display screen 102 are kept off to save power.

Figure 3B:
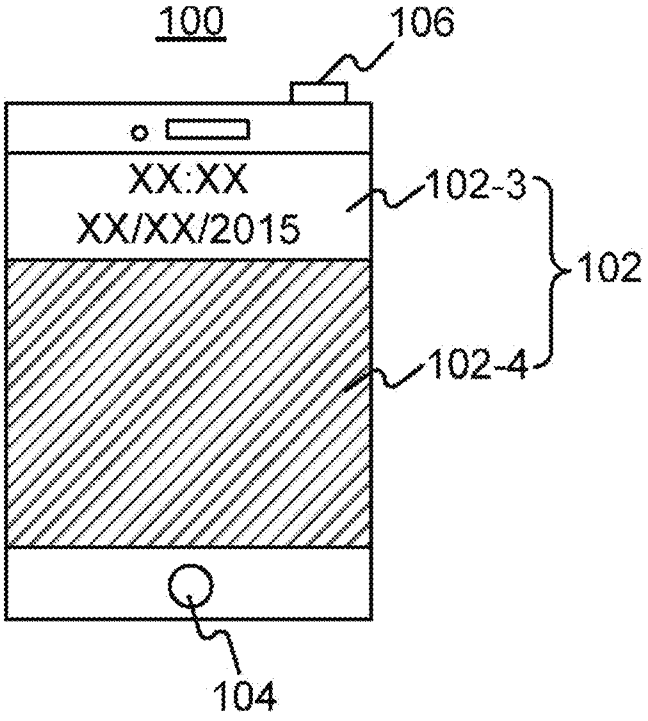

As illustrated in FIG. 3B, the first display area locates in a top fringe portion 102-3 of the display screen 102 and is turned on to display a predetermined user interface (such as an interface showing a current time and a current date) associated with a detected active event (such as a press on the control button 104 or the power button 106 for one time), and other portions 102-4 of the display screen 102 are kept off to save power.

In an embodiment of the present disclosure, the sizes of the first display area and the second display area may be automatically adjusted based on the content to be displayed, in order to conserve power flexibly.

In an embodiment of the present disclosure, the method may further include the following actions: detecting whether there is a user operation on the turned on display area within a first time period after the first event is detected; and turning off the turned on display area when no user operation is detected on the turned on display area. Therefore, the power consumption of the turned on display area may be saved.

It should be understood that, when a user operation (for example, slide, click, long hold for icons, etc.) is detected on the turned on display area, in order to response to the detected user operation, for example, the first display area can display a lock screen image, and wait for another user input such as a slide gesture to enable the electronic device 100 for further operation.

For a detected active event, in an embodiment, the action at the block 202 may specifically include the following: determining a type of a user operation corresponding to the first event, based on a determination that the first event is the active event; and acquiring, according to the determined type of the user operation, the predetermined user interface including at least one predetermined information item.

In an embodiment, the action at the block 202 may further include the following: when the user operation corresponding to the first event is a single press on a power button of the electronic device, determining whether there is at least one previous un-handled passive event; based on a determination that there is at least one previous un-handled passive event, generating a notification information item indicating all the un-handled passive events; and adding the notification information item into the predetermined user interface associated with the first event. Therefore, the user can review the un-handled passive events by pressing the power button of the electronic device 100.

Alternatively, in other embodiments, the notification information item may be not added into the predetermined user interface associated with the first event. The action at the block 204 may further include the following: turning on a second display area of the display screen to display the notification information item while the first display area is in an on state. That is, when there is at least one previous un-handled passive event, a single press on a power button of the electronic device will trigger the turning on of the first display area and the second display area.

In an embodiment, when the first event is the active event, after the action at the block 204 is performed, the method may further include the following actions: detecting whether there is a second event that will trigger partially turning on of the display screen within a second time period after the first event is detected, where the first display area is in an on state during the second time period; when the second event is detected, determining whether the second event belongs to one of the active event and the passive event; and acquiring a new predetermined user interface to be displayed according to the second event, and updating the first display area with the new predetermined user interface, based on a determination that the second event is the active event. In the embodiment, the second time period may be less than the first time period. That is, when a first active event and a second active event are detected in order, the information associated with the second active event to be displayed by the new predetermined user interface can replace the information associated with the first active event to be displayed by the predetermined user interface; when the information associated with the second active event displays, the information associated with the first active event disappears.

In an embodiment, a display priority of the active event is higher than that of the passive event. The method may further include the following actions: maintaining the predetermined user interface on the first display area, based on a determination that the second event is the passive event. That is, while the first display area is turned on to display the predetermined user interface associated with the previous active event, a user interface associated with a following passive event will not be displayed.

In an alternative embodiment, the method may further include the following actions: acquiring a new predetermined user interface to be displayed according to the second event, based on a determination that the second event is the passive event; and turning on the second display area to display the new predetermined user interface while the first display area is in an on state. That is, while the first display area is turned on to display the predetermined user interface associated with the previous active event, a following passive event will trigger the turning on of the second display area. It should be noted that, when there is no user operation detected on the turned on display area, the turned on first display area triggered by the previous active event may be turned off earlier than the turned on second display area triggered by the following passive event.

In an alternative embodiment, the method may further include the following actions: turning off the first display area, based on a determination that the second event is the passive event; acquiring a new predetermined user interface to be displayed according to the second event; and turning on the second display area to display the new predetermined user interface. That is, while the first display area is turned on to display the predetermined user interface associated with the previous active event, a following passive event will trigger the turning off of the first display area and the turning on of the second display area.

For a detected passive event, in an embodiment, the action at the block 202 may specifically include the following: determining an application running on the electronic device which is associated to the first event, based on a determination that the first event is the passive event; acquiring, according to the determined application, the predetermined user interface including at least one predetermined information item, where the at least one predetermined information item includes information indicating the type of the determined application. It should be noted that, the at least one predetermined information item can further include the information indicating the detecting time of the determined event.

In an embodiment, the plurality of passive events include a plurality of first passive events (such as a calendar reminder or a notification message) that are generated by their associated applications per se, and a plurality of second passive events (such as an incoming call or a text message) that are received by their associated applications from another electronic device.

The action at the block 202 may further include the following: when the first event is the first passive event, acquiring predetermined information associated with the first event, where the at least one predetermined information item further includes the acquired predetermined information; and when the first event is the second passive event, analyzing the first event and extracting content to be displayed from the first event, where the at least one predetermined information item further includes part or all of the extracted content.

It should be understood that, the predetermined information associated with the first passive event can be previously set by the user and stored in a storage medium of the electrical device 100.

In an embodiment, after the action at the block 205 is performed, the method may further include the following actions: determining whether there is at least one previous un-handled passive event after the first event is detected; generating a new user interface that includes a plurality of information items indicating all the un-handled passive events including the first event, based on a determination that there is at least one previous un-handled passive event; and updating the second display area with the new user interface.

In an embodiment, a display priority of the active event is higher than that of the passive event. When the first event is the passive event, after the action at the block 205 is performed, the method may further include the following actions: detecting whether there is a third event that will trigger partially turning on of the display screen within a third predetermined time period after the first event is detected, where the second display area is in an on state during the third predetermined time period; when the third event is detected, determining whether the third event belongs to one of the active event and the passive event; and acquiring a new predetermined user interface to be displayed according to the third event, and turning on the first display area to display the new predetermined user interface, based on a determination that the third event is the active event. In the embodiment, the third time period may be greater than or equal to the first time period. In the embodiment, the turned on second display area can be kept on or be turned off when the first display area is turned on.

In an embodiment, the method may further include the following actions: determining whether a display priority of the third event is higher than that of the first event, based on a determination that the third event is the passive event; updating the second display area with a new predetermined user interface associated with the third event at once, based on a determination that the display priority of the third event is higher than that of the first event; and maintaining the predetermined user interface on the second display area, based on a determination that the display priority of the third event is lower than that of the first event.

Figure 3C:
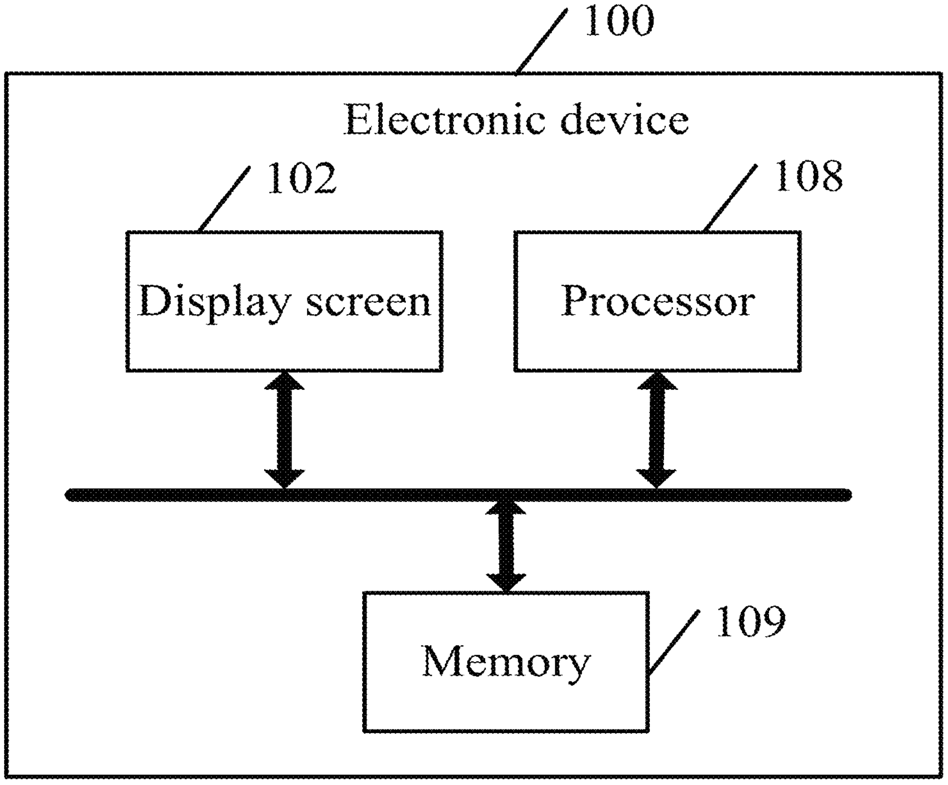
FIG. 3C is a schematic structural diagram of the electronic device according to an exemplary embodiment.

FIG. 3C is a schematic structural diagram of the electronic device 100 according to an exemplary embodiment of the present disclosure. As illustrated in FIG. 3C, the electronic device 100 includes a display screen 102, a processor 108, and a memory 109. In some embodiments of the present disclosure, the display screen 102, the processor 108, and the memory 109 may be coupled to each other via a bus or other means. The memory 109 is configured to store one or more computer executable instructions, and the one or more instructions are configured to be executed by the processor 108. The processor 108 is configured to execute the instructions to carry out part or all of the actions of any one of the methods described above and illustrated in above-described FIG. 2.

Figure 3D:
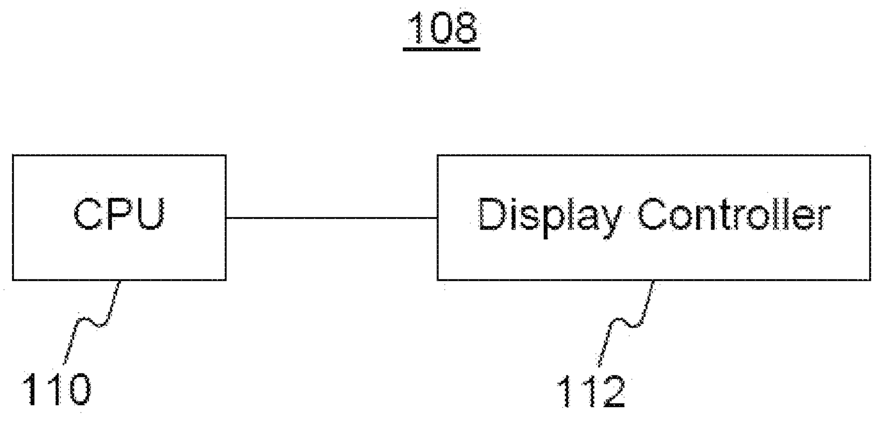
FIG. 3D is a schematic structural diagram of a processor of the electronic device according to an exemplary embodiment.

FIG. 3D is a schematic structural diagram of the processor 108 according to an exemplary embodiment. In an embodiment, the processor 108, that is a control logic of the electronic device 100, may include, as shown in FIG. 3D, a central processing unit (CPU) 110 and a display controller 112, which may be a function unit of the CPU 110 or a separate integrated circuit coupled between the CPU 110 and the display screen 102. Consistent with embodiments of the disclosure, the CPU 110 controls an overall operation of the electronic device 100, while the display controller 112 controls an operation of the display screen 102. For example, the display controller 112 controls the display screen 102 to turn on and off, and/or controls what contents are displayed on the display screen 102 and how they are displayed. In some embodiments, the display screen 102 includes a touch screen. In this scenario, the display controller 112 may also operate to process touching signals from the touch screen and generate corresponding instructions.

The display controller 112 may include various control units that control different components of the display screen. For example, the display screen 102 includes a plurality of display units arranged in an array, each of which may be individually controlled to turn on and off. By controlling the on and off of the display units and the amount of light emitting from the display units, an image can be displayed. To control the display units, the display controller 112 may include a timing control unit that generates control signals to be applied to the display units. In some embodiments, the display units of the display screen 102 do not generate light themselves, but rather can allow light to pass through. In this scenario, the display screen 102 also includes a backlight panel for generating light, and the display controller 112 further includes a backlight control unit to control the operation of the backlight panel.

Consistent with the present disclosure, the CPU 110 detects and analyzes the first event, and generates a CPU signal and sends it to the display controller 112, which then controls the operation of the display screen 102 according to the CPU signal.

In some embodiments, the display screen 102 includes a backlight-lit LCD, such as a light-emitting diode (LED) lit LCD. In such a display screen, backlight sources, such as LEDs, may be arranged as an array behind an LCD panel. Liquid-crystal (LC) cells in the LCD panel can be turned on and off to allow light to pass through or prevent light from passing through. In this scenario, the display controller 112 includes the backlight control unit configured to individually control the backlight sources. That is, instead of turning on and off all the backlight sources simultaneously, the backlight control unit may be configured to turn on and off each individual backlight source separately. In some embodiments, the backlight sources may be divided into several groups, each of which includes multiple backlight sources. The backlight control unit may also be configured to turn on and off each individual group separately.

Figure 4A:
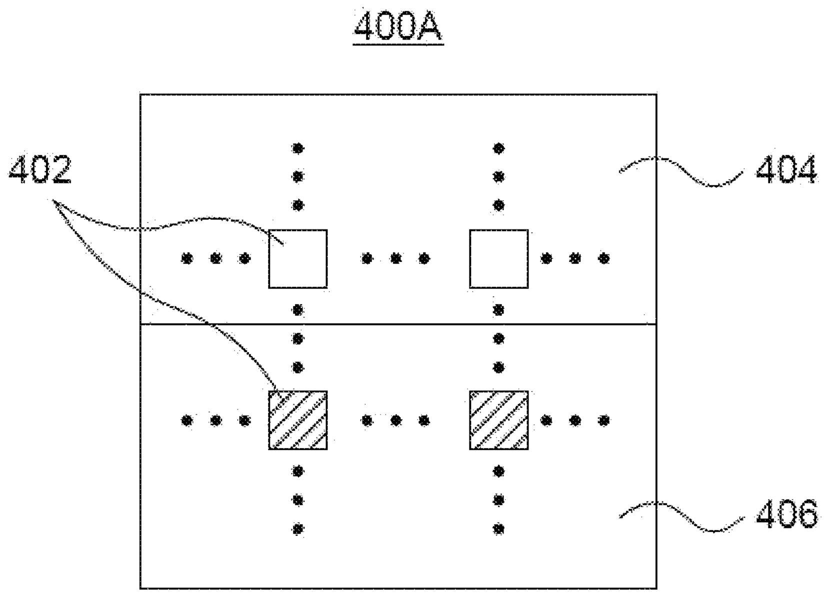
FIG. 4A schematically shows a backlight panel in an LCD display screen according to an exemplary embodiment.

FIG. 4A schematically shows an exemplary backlight panel 400A consistent with embodiments of the present disclosure. The backlight panel 400A may be installed in the display screen 102 when the display screen 102 includes an LCD display screen. The backlight panel 400A is positioned behind an LCD panel (not shown in FIG. 4A) and includes a plurality of backlight units 402 arranged in an array. Each backlight unit 402 can be separately controlled by the backlight control unit, and may include one or more backlight resources, such as LEDs.

Figure 4B:
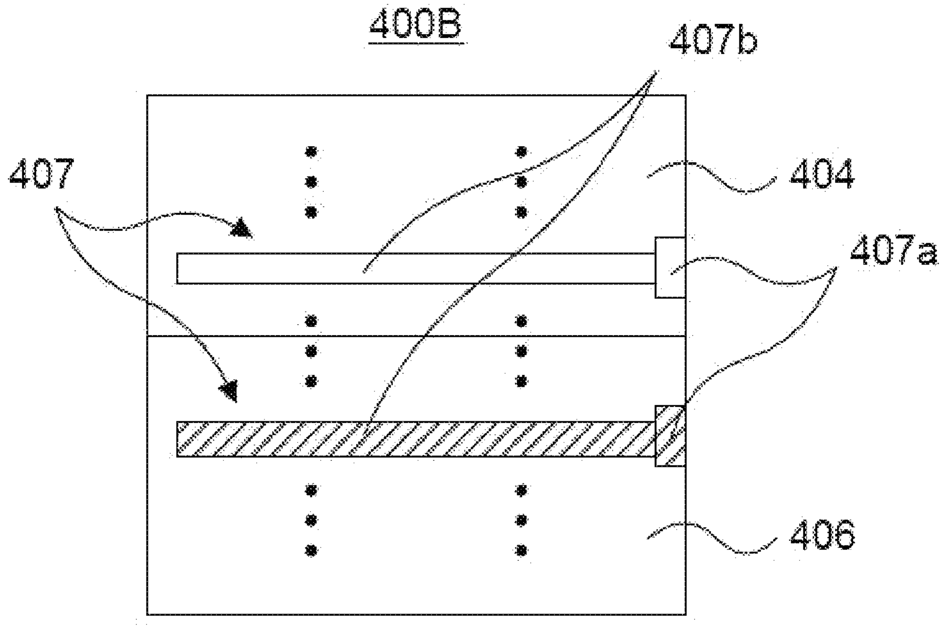
FIG. 4B schematically shows a backlight panel in an LCD display screen according to another exemplary embodiment.

FIG. 4B schematically shows another exemplary backlight panel 400B consistent with embodiments of the present disclosure. The backlight panel 400B is similar to the backlight panel 400A, except that the backlight panel 400B includes a plurality of backlight units 407 arranged in a row, instead of the backlight units 402 arranged in an array. The backlight panel 400B may also be installed in the display screen 102 when the display screen 102 includes an LCD display screen, and be positioned behind an LCD panel (not shown in FIG. 4A). Each backlight unit 407 includes one or more backlight resources 407*a*, such as LEDs, and one or more waveguides 407*b*. The backlight resources 407*a* may be arranged at one or more edges of the backlight panel 400B. The waveguides 407*b* convey the light emitted by the backlight resources 407*a* to the entire backlight panel 400B. Similar to the backlight units 402, each of the backlight units 407 can be separately controlled by the backlight control unit.

Consistent with the present disclosure, according to the controlling signal from the CPU 110, the backlight control unit operates to turn on the backlight sources of the backlight units (the backlight units 402 in FIG. 4A or the backlight units 407 in FIG. 4B) in a first portion 404 of the backlight panel (the backlight panel 400A in FIG. 4A or the backlight panel 400B in FIG. 4B), and keep off the backlight sources of the backlight units in a second portion 406 of the backlight panel. The first portion 404 corresponds to the portion of the display screen 102 that needs to be turned on to display information, such as the portion 102-1 in FIG. 3A or the portion 102-3 in FIG. 3B. The second portion 406 corresponds to the portion of the display screen 102 that does not need to be turned on, such as the portion 102-2 in FIG. 3A or the portion 102-4 in FIG. 3B.

In an LCD display, each LC cell in the LCD panel may be controlled by one or more thin-film transistors (TFTs). In some embodiments, instead of or in addition to partially turning on the backlight sources, the display controller 112 may also control to partially turn on the LC cells by individually controlling the on and off of the TFTs.

Figure 4C:
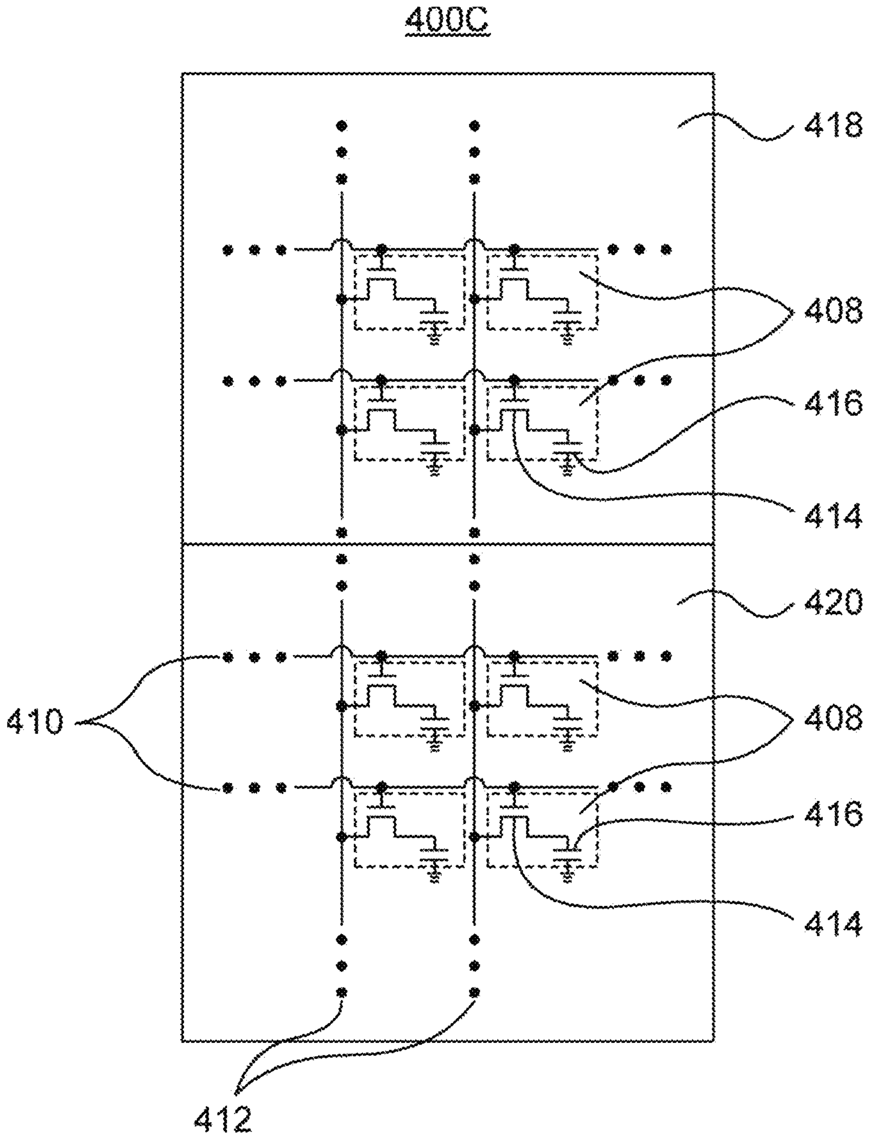
FIG. 4C schematically shows an LCD panel in the LCD display screen according to an exemplary embodiment.

FIG. 4C schematically shows an exemplary LCD panel 400C consistent with embodiments of the present disclosure. The LCD panel 400C may be installed in the display screen 102 when the display screen 102 includes an LCD display screen. The LCD panel 400C is positioned in front of a backlight panel (not shown in FIG. 4C) and includes a plurality of LCD units 408 arranged in an array. Each LCD unit 408 is coupled between a scan line 410 and a data line 412, and includes a TFT 414 coupled to an LC cell 416. By applying various signals to the scan lines 410 and the data lines 412, the display controller 112 can control the on and off of the TFTs 414, and thus the on and off of the LC cells 416. Such various signals can be generated by the timing control unit in the display controller 112.

According to the present disclosure, the LCD panel 400C may include additional components not shown in FIG. 4C. For example, each LCD unit 408 may further include a compensation circuit.

Consistent with the present disclosure, according to the controlling signal from the CPU 110, the timing control unit operates to only provide signals to the TFTs 414 in a first portion 418 of the LCD panel 400C but not the TFTs 414 in a second portion 420 of the LCD panel 400C. As such, the LC cells 416 in the first portion 418 of the LCD panel 400C are turned on while the LC cells 416 in the second portion 420 of the LCD panel 400C are kept off. The first portion 418 of the LCD panel 400C corresponds to the portion of the display screen 102 that needs to be turned on to display information, such as the portion 102-1 in FIG. 3A or the portion 102-3 in FIG. 3B. The second portion 420 of the LCD panel 400C corresponds to the portion of the display screen 102 that does not need to be turned on, such as the portion 102-2 in FIG. 3A or the portion 102-4 in FIG. 3B.

The above scheme of partially turning on LC cells applies to an LCD display screen that does not have a plurality of backlight sources, an LCD display screen having backlight source(s) arranged at one or more sides of the LCD panel, or an LCD display screen having backlight sources arranged in an array across the LCD panel. Since turning on an LC cell may require applying a voltage across the LC cell and thus consumes power, keeping off the LC cells that are not needed for displaying information also reduces the power consumption by the display screen 102.

In some embodiments, the display screen 102 includes an AMOLED panel. An AMOLED panel includes a plurality of OLEDs arranged in an array. Each OLED can be individually controlled to emit light.

Figure 5A:
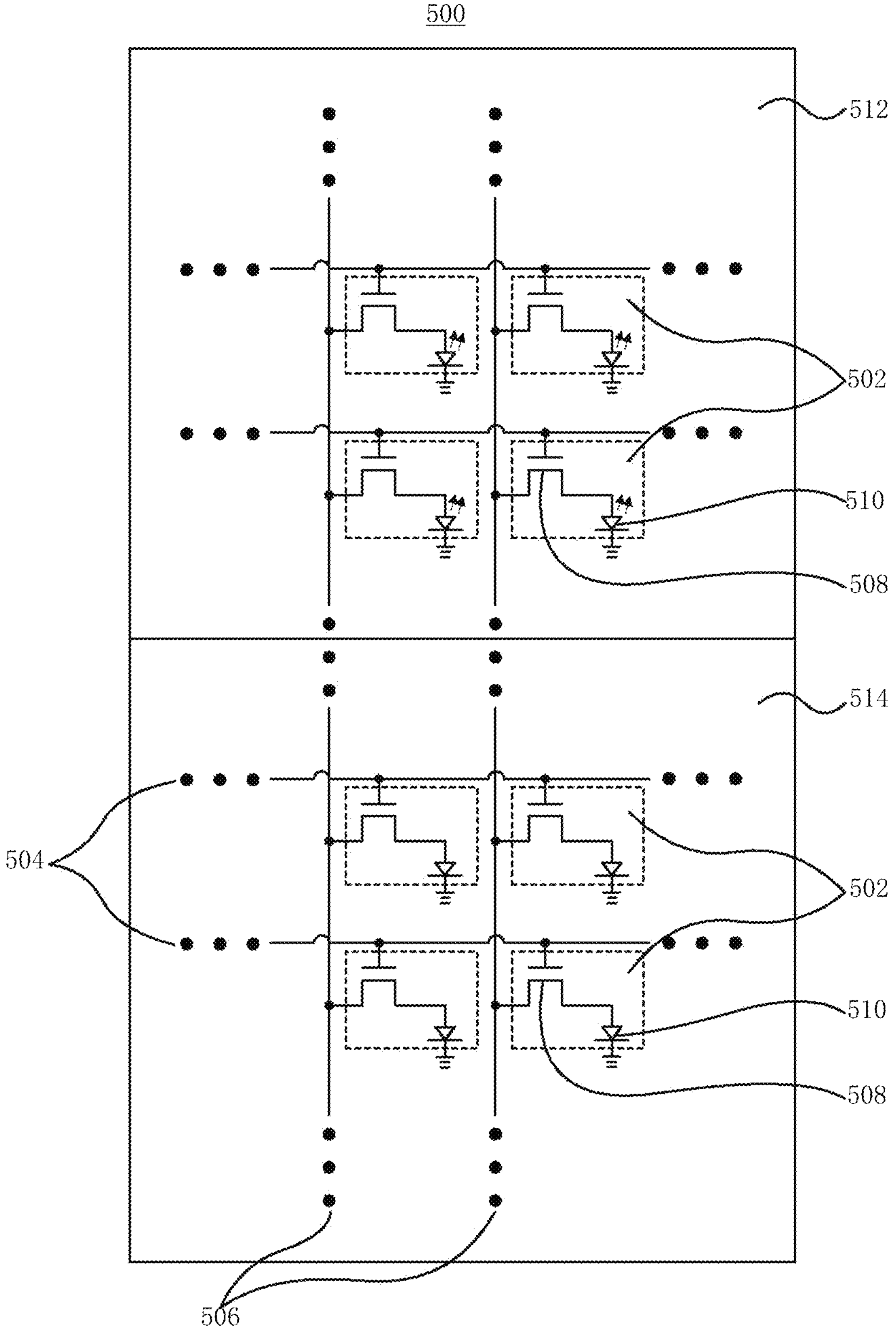
FIG. 5A schematically shows an organic light-emitting diode (OLED) panel in an active-matrix OLED (AMOLED) display screen according to an exemplary embodiment.

FIG. 5A schematically shows an exemplary AMOLED panel 500 consistent with embodiments of the present disclosure. The AMOLED panel 500 may be installed in the display screen 102 when the display screen 102 includes an AMOLED display screen. The AMOLED panel 500 includes a plurality of AMOLED units 502 arranged in an array. Each AMOLED unit 502 is coupled between a scan line 504 and a data line 506, and includes a TFT 508 and an OLED 510. By applying various signals to the scan lines 504 and the data line 506, the display controller 112 can control the on and off of the TFTs 508 individually, and thus control the on and off of the OLEDs 510 individually. Such various signals can be generated by the timing control unit in the display controller 112.

Consistent with the present disclosure, according to the controlling signal from the CPU 110, the timing control unit operates to provide signals to the TFTs 508 in a first portion 512 of the AMOLED panel 500, but not the TFTs 508 in a second portion 514 of the AMOLED panel 500. As such, the OLEDs 510 in the first portion 512 of the AMOLED panel 500 are turned on, while the OLEDs 510 in the second portion 514 of the AMOLED panel 500 are kept off. The first portion 512 of the AMOLED panel 500 corresponds to the portion of the display screen 102 that needs to be turned on to display information, such as the portion 102-1 in FIG. 3A or the portion 102-3 in FIG. 3B. The second portion 514 of the AMOLED panel 500 corresponds to the portion of the display screen 102 that does not need to be turned on, such as the portion 102-2 in FIG. 3A or the portion 102-4 in FIG. 3B.

Figure 5B:
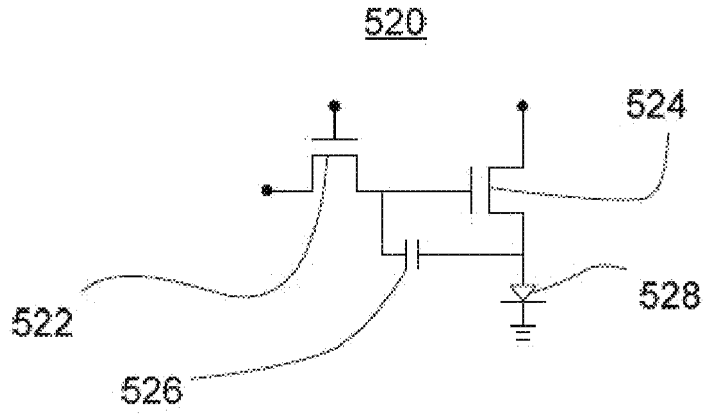
FIG. 5B schematically shows an AMOLED unit according to another exemplary embodiment.

It is noted that the AMOLED units 502 shown in FIG. 5A are a simplified example of AMOLED units. The AMOLED units according to the present disclosure may have a more complex structure. For example, FIG. 5B schematically shows another exemplary AMOLED unit 520. The AMOLED unit 520 includes a first TFT 522, a second TFT 524, a capacitor 526, and an OLED 528. In some embodiments, the AMOLED unit may have more than one capacitor, and may also have a compensation circuit.

In some embodiments, the display screen 102 includes an e-ink panel. An e-ink panel includes a plurality of pixels arranged in an array. Each pixel can be individually controlled to reflect light of different colors.

Figure 6:
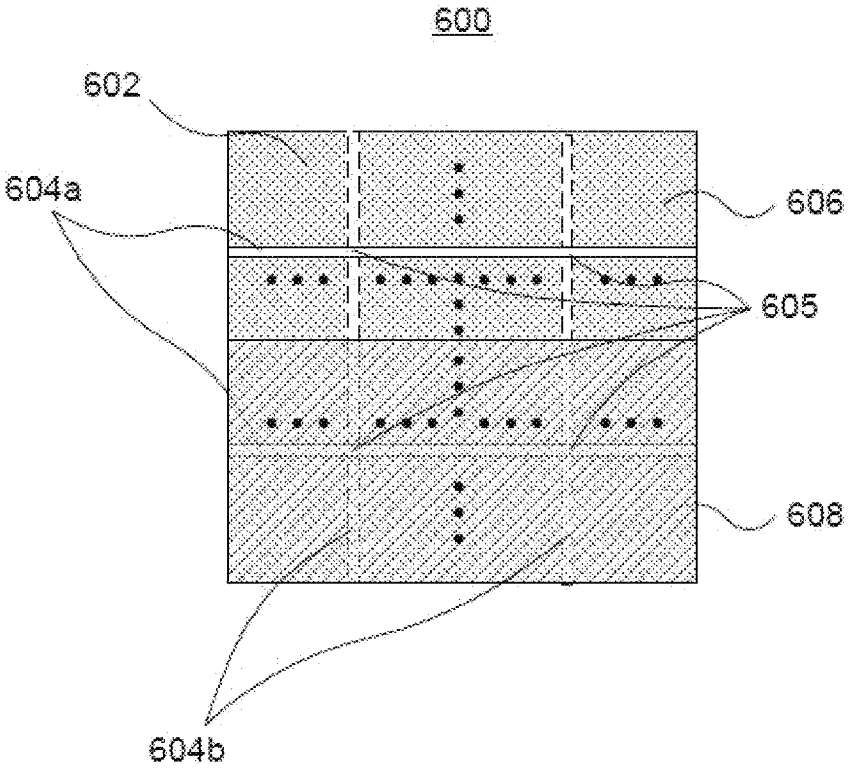
FIG. 6 schematically shows an e-ink panel in an e-ink display screen according to an exemplary embodiment.

FIG. 6 schematically shows an exemplary e-ink panel 600 consistent with embodiments of the present disclosure. The e-ink panel 600 may be installed in the display screen 102 when the display screen 102 includes an e-ink display screen. The e-ink panel 600 includes a plurality of particles 602 dispersed between two plates (not shown). In some embodiments, each particle 602 has different color on different sides, with different sides facing up (such as the direction perpendicular to the drawing sheet) when different electric fields are applied so that different colors can be displayed. In some embodiments, the particles 602 float in a liquid filled between the two plates, and migrate to one of the two plates depending on the applied field so that different colors can be displayed.

As shown in FIG. 6, the e-ink panel 600 further includes a plurality of first electrodes 604*a* and a plurality of second electrodes 604*b* arranged crossing each other. Cross-points 605 between the first and the second electrodes 604 constitute pixels of the e-ink panel 600. By applying various signals to the first and second electrodes 604*a* and 604*b*, the display controller 112 can individually control the electric field, and thus the color, at each cross-point 605. Such various signals can be generated by the timing control unit in the display controller 112.

Consistent with the present disclosure, according to the controlling signal from the CPU 110, the display controller 112 operates to apply voltages to the electrodes in a first portion 606 of the e-ink panel 600, and not to the electrodes in a second portion 608 of the e-ink panel 600. The first portion 606 corresponds to the portion of the display screen 102 that needs to be turned on to display information, such as the portion 102-1 in FIG. 3A or the portion 102-3 in FIG. 3B. The second portion 608 corresponds to the portion of the display screen 102 that does not need to be turned on, such as the portion 102-2 in FIG. 3A or the portion 102-4 in FIG. 3B.

It is noted that the e-ink panel 600 shown in FIG. 6 is for illustration purpose only. An e-ink panel consistent with the present disclosure may have a more complicated structure. For example, TFTs may be employed in the e-ink panel to control the electric field at the pixels.

Consistent with the present disclosure, the electronic device 100 may also include a non-transitory computer-readable storage medium, such as a memory, that stores data for supporting the operation of the electronic device 100. The storage medium is coupled to the CPU 110 and/or the display controller 112, and stores instructions that cause the electronic device 100 to, for example, operate in consistence with embodiments of the present disclosure. For example, the instructions may cause the CPU 110 and/or the display controller 112 to execute methods consistent with embodiments of the present disclosure, such as those described above. The storage medium may include, for example, a volatile or a non-volatile memory device, or a combination thereof, such as a static random access memory (SRAM), a read-only memory (ROM), a programmable read-only memory (PROM), an erasable programmable read-only memory (EPROM), an electrically erasable programmable read-only memory (EEPROM), a magnetic memory, a flash memory, or a magnetic or optical disk.

Other embodiments of the present disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for controlling a display screen of an electronic device, comprising:

detecting a first event that will trigger partially turning on of the display screen while the display screen is in an off state;

acquiring a predetermined user interface to be displayed according to the first event;

determining whether the first event belongs to one of the following: (1) an active event resulting from a user operation on the electronic device, and (ii) a passive event that is independent of a user operation on the electronic device;

turning on a first display area of the display screen to display the acquired predetermined user interface, based on a determination that the first event is the active event, wherein the first display area corresponds to a plurality of active events, and the predetermined user interfaces associated with the plurality of active events are all displayed on the first display area; and turning on a second display area of the display screen to display the acquired predetermined user interface, based on a determination that the first event is the passive event, wherein the second display area corresponds to a plurality of passive events, and the predetermined user interfaces associated with the plurality of passive events are all displayed on the second display area.

2. The method of claim 1, further comprising:

detecting whether there is a user operation on the turned on display area within a first time period after the first event is detected; and turning off the turned on display area when no user operation is detected on the turned on display area.

3. The method of claim 2, wherein the acquiring a predetermined user interface to be displayed according to the first event comprises:

determining a type of a user operation corresponding to the first event, based on a determination that the first event is the active event; and acquiring, according to the determined type of the user operation, the predetermined user interface comprising at least one predetermined information item.

4. The method of claim 1, wherein the acquiring a predetermined user interface to be displayed according to the first event further comprises:

when the user operation corresponding to the first event is a single press on a power button of the electronic device, determining whether there is at least one previous un-handled passive event;

based on a determination that there is at least one previous un-handled passive event, generating a notification information item indicating all the un-handled passive events; and adding the notification information item into the predetermined user interface associated with the first event.

5. The method of claim 3, further comprising:

based on a determination that the first event is the active event, further detecting whether there is a second event that will trigger partially turning on of the display screen within a second time period after the first event is detected, wherein the first display area is in an on state during the second time period;

when the second event is detected, determining whether the second event belongs to one of the active event and the passive event; and acquiring a new predetermined user interface to be displayed according to the second event, and updating the first display area with the new predetermined user interface, based on a determination that the second event is the active event.

6. The method of claim 5, wherein the method further comprises one of the following:

maintaining the predetermined user interface on the first display area, based on a determination that the second event is the passive event;

acquiring a new predetermined user interface to be displayed according to the second event, and turning on the second display area to display the new predetermined user interface while the first display area is in an on state; and turning off the first display area, acquiring a new predetermined user interface to be displayed according to the second event, and turning on the second display area to display the new predetermined user interface.

7. The method of claim 2, wherein the acquiring a predetermined user interface to be displayed according to the first event comprises:

determining an application running on the electronic device which is associated to the first event, based on a determination that the first event is the passive event;

acquiring, according to the determined application, the predetermined user interface comprising at least one predetermined information item, wherein the at least one predetermined information item comprises information indicating the type of the determined application.

8. The method of claim 7, wherein the plurality of passive events comprise a plurality of first passive events that are generated by their associated applications per se and a plurality of second passive events that are received by their associated applications from another electronic device; the acquiring a predetermined user interface to be displayed according to the first event further comprises:

when the first event is one of the plurality of first passive events, acquiring predetermined information associated with the first event, wherein the at least one predetermined information item further comprises the acquired predetermined information; and when the first event is one of the plurality of second passive events, analyzing the first event and extracting content to be displayed from the first event, wherein the at least one predetermined information item further comprises part or all of the extracted content.

9. The method of claim 8, further comprising:

determining whether there is at least one previous un-handled passive event after the first event is detected;

generating a new user interface that comprises a plurality of information items indicating all un-handled passive events comprising the first event and the at least one previous un-handled passive event, based on a determination that there is at least one previous un-handled passive event; and updating the second display area with the new user interface.

10. The method of claim 8, wherein a display priority of the active event is higher than that of the passive event, and the method further comprises:

based on a determination that the first event is the passive event, further detecting whether there is a third event that will trigger partially turning on of the display screen within a third predetermined time period after the first event is detected, wherein the second display area is in an on state during the third predetermined time period;

when the third event is detected, determining whether the third event belongs to one of the active event and the passive event; and acquiring a new predetermined user interface to be displayed according to the third event, and turning on the first display area to display the new predetermined user interface, based on a determination that the third event is the active event.

11. The method of claim 10, further comprising:

determining whether a display priority of the third event is higher than that of the first event, based on a determination that the third event is the passive event;

updating the second display area with a new predetermined user interface associated with the third event at once, based on a determination that the display priority of the third event is higher than that of the first event; and maintaining the predetermined user interface on the second display area, based on a determination that the display priority of the third event is lower than that of the first event.

12. An electronic device, comprising:

a display screen;

a processor; and a computer readable storage, coupled to the processor and storing at least one computer executable instruction thereon, which when executed by the processor, cause the processor to carry out actions, comprising:

detecting a first event that will trigger partially turning on of the display screen while the display screen is in an off state;

acquiring a predetermined user interface to be displayed according to the first event;

determining whether the first event belongs to one of the following: (1) an active event resulting from a user operation on the electronic device, and (ii) a passive event that is independent of a user operation on the electronic device;

turning on a first display area of the display screen to display the acquired predetermined user interface, based on a determination that the first event is the active event, wherein the first display area corresponds to a plurality of active events, and the predetermined user interfaces associated with the plurality of active events are all displayed on the first display area; and turning on a second display area of the display screen to display the acquired predetermined user interface, based on a determination that the first event is the passive event, wherein the second display area corresponds to a plurality of passive events, and the predetermined user interfaces associated with the plurality of passive events are all displayed on the second display area.

13. The electronic device of claim 12, wherein the processor is further caused to carry out actions, comprising:

when the user operation corresponding to the first event is a single press on a power button of the electronic device, determining whether there is at least one previous un-handled passive event;

based on a determination that there is at least one previous un-handled passive event, generating a notification information item indicating all the un-handled passive events; and adding the notification information item into the predetermined user interface associated with the first event.

14. The electronic device of claim 12, wherein the processor carrying out the action of acquiring a predetermined user interface to be displayed according to the first event is caused to carry out actions, comprising:

determining a type of a user operation corresponding to the first event, based on a determination that the first event is the active event; and acquiring, according to the determined type of the user operation, the predetermined user interface comprising at least one predetermined information item.

15. The electronic device of claim 14, wherein the processor is further caused to carry out actions, comprising:

based on a determination that the first event is the active event, further detecting whether there is a second event that will trigger partially turning on of the display screen within a second time period after the first event is detected, wherein the first display area is in an on state during the second time period;

when the second event is detected, determining whether the second event belongs to one of the active event and the passive event; and acquiring a new predetermined user interface to be displayed according to the second event, and updating the first display area with the new predetermined user interface, based on a determination that the second event is the active event.

16. The electronic device of claim 13, wherein the processor carrying out the action of acquiring a predetermined user interface to be displayed according to the first event is caused to carry out actions, comprising:

determining an application running on the electronic device which is associated to the first event, based on a determination that the first event is the passive event;

acquiring, according to the determined application, the predetermined user interface comprising at least one predetermined information item, wherein the at least one predetermined information item comprises information indicating the type of the determined application.

17. The electronic device of claim 16, wherein the plurality of passive events comprise a plurality of first passive events that are generated by their associated applications per se and a plurality of second passive events that are received by their associated applications from another electronic device; the processor carrying out the action of acquiring a predetermined user interface to be displayed according to the first event is further caused to carry out actions, comprising:

when the first event is one of the plurality of first passive events, acquiring predetermined information associated with the first event, wherein the at least one predetermined information item further comprises the acquired predetermined information; and when the first event is one of the plurality of second passive events, analyzing the first event and extracting content to be displayed from the first event, wherein the at least one predetermined information item further comprises part or all of the extracted content.

18. The electronic device of claim 17, wherein a display priority of the active event is higher than that of the passive event, and the processor is further caused to carry out actions, comprising:

based on a determination that the first event is the passive event, further detecting whether there is a third event that will trigger partially turning on of the display screen within a third predetermined time period after the first event is detected, wherein the second display area is in an on state during the third predetermined time period;

when the third event is detected, determining whether the third event belongs to one of the active event and the passive event; and acquiring a new predetermined user interface to be displayed according to the third event, and turning on the first display area to display the new predetermined user interface, based on a determination that the third event is the active event.

19. The electronic device of claim 18, wherein the processor is further caused to carry out actions, comprising:

determining whether a display priority of the third event is higher than that of the first event, based on a determination that the third event is the passive event;

updating the second display area with a new predetermined user interface associated with the third event at once, based on a determination that the display priority of the third event is higher than that of the first event; and maintaining the predetermined user interface on the second display area, based on a determination that the display priority of the third event is lower than that of the first event.

20. A non-transitory computer-readable storage medium storing computer programs which, when executed by a processor, cause the processor to carry out actions:

detecting a first event that will trigger partially turning on of a display screen of an electronic device while the display screen is in an off state;

acquiring a predetermined user interface to be displayed according to the first event;

determining whether the first event belongs to one of the following: (1) an active event resulting from a user operation on the electronic device, and (ii) a passive event that is independent of a user operation on the electronic device;

turning on a first display area of the display screen to display the acquired predetermined user interface, based on a determination that the first event is the active event, wherein the first display area corresponds to a plurality of active events, and the predetermined user interfaces associated with the plurality of active events are all displayed on the first display area; and turning on a second display area of the display screen to display the acquired predetermined user interface, based on a determination that the first event is the passive event, wherein the second display area corresponds to a plurality of passive events, and the predetermined user interfaces associated with the plurality of passive events are all displayed on the second display area.

* * * * *